United States Patent [19]

Myers et al.

[11] 4,233,438

[45] Nov. 11, 1980

[54] HETEROPOLYSACCHARIDE BIOPOLYMER

[75] Inventors: Philip A. Myers, Windlesham; David J. Westlake, Woking, both of England

[73] Assignee: The British Petroleum Company Limited, England

[21] Appl. No.: 819,579

[22] Filed: Jul. 27, 1977

[30] Foreign Application Priority Data

Jul. 29, 1976 [GB] United Kingdom ............... 31639/76

[51] Int. Cl.$^3$ .......................... C08B 37/00; C07H 1/08
[52] U.S. Cl. ........................................ 536/1; 424/181; 435/104; 252/8.5 R; 252/8.55 R; 252/89.1; 252/309; 252/311
[58] Field of Search .............................. 536/1; 195/31

[56] References Cited

U.S. PATENT DOCUMENTS

| 3,894,976 | 7/1975 | Kang et al. | 536/1 |
|---|---|---|---|
| 3,923,782 | 12/1975 | Finn et al. | 536/1 |
| 3,930,947 | 1/1976 | Morinaga et al. | 536/1 |

*Primary Examiner*—Johnnie R. Brown
*Attorney, Agent, or Firm*—Jacobs & Jacobs

[57] ABSTRACT

A fermentation process for the production of microbial biomass and a heteropolysaccharide biopolymer using methane as a carbon source. The biomass is suitable for use as a feedstuff and the polymer can be used as a thickening agent e.g. in foods or in the oil industry for use in drilling muds and to assist the recovery of subterranean deposits of oil. The process comprises cultivating at least one strain of a methane utilizing and extracellular heteropolysaccharide biopolymer forming bacterium of the group Methylomonas in a broth comprising an aqueous nutrient medium and a utilizable nitrogen source in the presence of a gas containing methane as a carbon source and a gas containing free oxygen and recovering biomass and heteropolysaccharide biopolymer from the cultivated broth.

1 Claim, 1 Drawing Figure

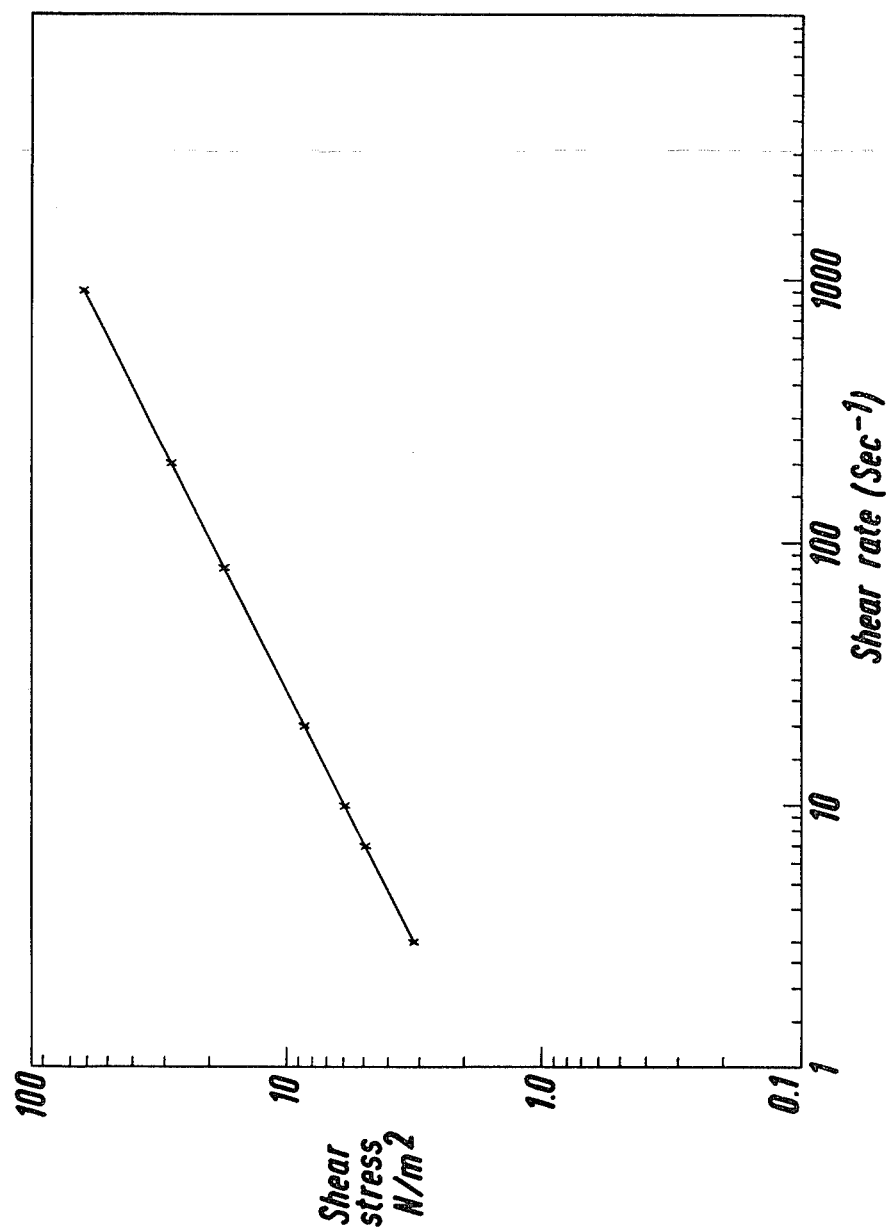

HETEROPOLYSACCHARIDE BIOPOLYMER

The present invention relates to a fermentation process for the production of microbial biomass and a heteropolysaccharide biopolymer using a gas containing methane as a carbon source. The invention also relates to micro-organisms which produce the microbial biomass and the biopolymer.

Fermentation processes are known for the production of microbial biomass using a gas containing methane as a carbon source. The term gas containing methane is used throughout this specification to include methane, and any gas in which methane is present such as for example natural gas or field gas. The biomass thus produced consists essentially of microbial cells. The micro-organisms are usually unicellular. This type of biomass is often described as single cell protein because each cell comprises a substantial proportion of protein which is contained within a cell wall. The biomass can be used as a feedstuff. Alternatively the protein can be extracted from the cells prior to use.

Processes have been developed for forming the biomass or protein recovered therefrom into structured products which simulate meat. Red dyes have been added to give the product a meat-like appearance. These processes for forming a structured product are often not entirely satisfactory and the addition of dye adds to its cost. Furthermore the meat-like appearance is often lost when the product is subjected to heat treatment in operations such as canning.

Fermentation processes are also known for the production by micro-organisms of polysaccharide biopolymers. The carbon source for the micro-organisms used in such processes is normally a carbohydrate, e.g. glucose and/or sucrose. However processes using methanol or formaldehyde as a carbon source have been reported. The processes described in the literature are normally batch processes. The microbial polymers produced by these processes have many industrial uses, particularly as thickening agents, e.g. in foods and in the oil industry, for use in drilling muds and to assist the recovery of subterranean deposits of crude oil.

Accordingly the present invention is a process for the production of microbial biomass and a heteropolysaccharide biopolymer which comprises cultivating in a broth comprising an aqueous nutrient medium and a utilisable nitrogen source in the presence of a gas containing methane as a carbon source and a gas containing free oxygen, at least one strain of a methane-utilising and extra cellular heteropolysaccharide biopolymer forming bacterium of the group Methylomonas and recovering microbial biomass and heteropolysaccharide biopolymer from the broth.

The process can be operated aseptically or non-aseptically. When the process is operated non-aseptically a mixture of micro-organisms can be present. The mixture can comprise at least one strain of a methane utilising and heteropolysaccharide biopolymer forming bacterium of the group Methylomonas and at least one strain of a micro-organism which can utilise organic substances formed by the methane utilising and heteropolysaccharide biopolymer forming micro-organism.

The process can be operated in such a manner as to recover from the broth either separately or simultaneously on the one hand microbial biomass and on the other hand heteropolysaccharide biopolymer.

The methane utilising and heteropolysaccharide biopolymer forming Methylomonas and the associated micro-organism or micro-organisms can be obtained by a non-aseptic continuous enrichment technique such as for example that described by Sheehan and Johnson. Applied Microbiology 1971, Vol. 21, at p. 512.

The methane utilising biopolymer forming micro-organism is a strain of bacterium selected from the group Methylomonas as described by Whittenbury et al in the Journal of General Microbiology 1970, Vol. 61, at page 213. Preferably the strain can contain or form a pink/red pigment which imparts a meat like colour to the biomass. Most suitably the strain can utilise elemental nitrogen as a nitrogen source. We have deposited a new and particularly suitable strain in the National Collection for Industrial Bacteria, Aberdeen, Scotland where it has been given the NCIB number 11221. A description of the characteristics of this strain is given in the Examples of this specification. Methylomonas strain NCIB 11221 can form a pink/red pigment which imparts a meat like colour to the biomass. The strain can utilise elemental nitrogen as a nitrogen source.

The micro-organism or micro-organisms which can utilise organic substances formed by the methane utilising and biopolymer forming strain of Methylomonas may also form a biopolymer and it may be pigment forming. Normally the micro-organism is a bacterium. Where the micro-organism is a bacterium it is usually a non-motile or motile Gram negative rod which can grow aerobically on a medium such as nutrient agar. Such bacteria can be selected from, for example, the genera Flavobacterium and Pseudomonas. We have deposited new and particularly suitable strains of such bacteria in the National Collection for Industrial Bacteria where they have been given numbers NCIB. 11229, 11230, 11254, 11255, 11256, 11257 and 11258. A description of the characteristics of each of these strains is given in the Examples. When the process is operated nonaseptically a mixture of micro-organisms comprising two or more of these strains is usually present. The proportion by weight of cells (dry weight) of the methane utilising and biopolymer forming strain or strains of Methylomonas relatively to the weight of cells of the remaining bacteria under continuous steady state conditions of culture can be in the range 50 to 98 percent and preferably in the range 75 to 95 percent. The relative proportions of the types of micro-organisms present in the broth remain stable for prolonged periods of steady state continuous operation. The organic substances utilised by these bacteria are lysis or metabolic products of the methane utilising bacterium.

We have isolated and deposited with the National Culture for Industrial bacteria a subculture of a mixture of micro-organisms which can be used in the present process. The subculture has been given the number NCIB 11253. The culture comprises essentially a methane and elemental nitrogen utilising and biopolymer forming species of Methylomonas strain no. NCIB 11221 and the following micro-organism which can utilise organic compounds formed by the Methylomonas species; a species of the genus Flavobacterium strain no. NCIB 11229, and a small number of unidentified bacteria which include at least two strains which were found to be species of the genera Pseudomonas and Alcaligenes, a strain tentatively identified as Pseudomonas maltophilia.

Any aqueous nutrient medium which is known to be suitable for the cultivation of methane-utilising micro-organisms can be used as the basic component of the fermentation broth. Elements which are usually present are sulphur, phosphorus, magnesium, potassium and calcium. Phosphorus is usually present as phosphate ions, sulphur as sulphate ions and potassium, magnesium, and calcium as the sulphate, chloride or nitrate salts. The medium usually contains traces of other elements e.g. sodium, manganese, copper iron, zinc, cobalt, molybdenum, nickel and boron which are present in the form of suitable salts. The nitrogen source is usually in the form of combined nitrogen, e.g. as ammonium or nitrate ions. When nitrate is used it can be added to or incorporated in the aqueous nutrient medium as the salt or as nitric acid. When ammonion ions are used they are usually added to the broth separately to the medium as ammonia gas or ammonium hydroxide solution. When the micro-organisms are capable of utilising elemental nitrogen, e.g. the nitrogen present in the air as a nitrogen source it can be used either alone or to supplement combined nitrogen. Our experience indicates that all methane utilising and biopolymer forming bacteria of the group Methylomonas can utilise elemental nitrogen. When Methylomonas strain NCIB 11221 is present the nitrogen source is preferably in the form of a nitrate supplemented by the elemental nitrogen present in the air.

Suitable gases containing methane include methane, natural gas, field gas, and the methane-containing gas produced by anaerobic digestion processes.

Preferably the process can be started up by inoculating a fermenter either with a subculture of the methane utilising and biopolymer forming strain or when a mixture of micro-organisms is required with a subculture of each of the separate single isolates which form the components of the mixture or with a subculture some or all the components of the mixture. The isolates can be stored on agar slopes or freeze dried.

Operation can be either batch or continuous or involve both continuous and batch stages. It is preferred to operate continuously under steady state conditions, with or without a subsequent stage of batch culture.

The pH of the broth during cultivation is usually maintained in the range 5.0 to 8.0 and preferably in the range 6.0 to 7.0. An alkali such as, for example, a hydroxide of an alkali metal or ammonia or ammonium hydroxide can be added to the broth as required to maintain the desired pH. Where ammonia or ammonium hydroxide is used to control the pH the ammonium ions can also serve as a nitrogen source. Ammonium ions when present in concentrations above certain threshold levels can inhibit growth or decrease the rate of growth of the methane-utilising and biopolymer forming bacterium. The ammonium ion concentration in the broth should not be allowed to exceed 100 milligrams per liter and preferably should be in the range 2 to 50 milligrams per liter.

The temperature can be in the range 25° to 55° C. The process is usually operated at a temperature in the range 28° C. to 35° C.

The gas containing free oxygen is normally air. In continuous operation at commercially acceptable production rates using methane/air mixtures the proportion of the gas containing methane to air supplied to the broth is normally in a range which results in a ratio of from 1 volume of methane to 2 volumes of oxygen to 2 volumes of methane to 1 volume of oxygen. The preferred ratio is 1 volume of methane to 1 volume of oxygen.

We have found that the use of a two stage process can facilitate biopolymer formation. In a first stage cultivation is continuous and cultivated broth from the first stage is treated in a second stage to batch cultivation in the presence of a gas containing methane and a gas containing oxygen under conditions whereby growth of the methane utilising and biopolymer forming strain of Methylomonas is limited by restriction or absence of an essential nutrient other than methane or oxygen. For example this essential nutrient can be the nitrogen source e.g. nitrate.

When one fermenter is used or when the process is carried out in two stages the fermenter or fermenters can and normally do have one or more impellers and can have a draft-tube system to achieve good mixing of the broth and high gas transfer rates.

The biomass can be recovered from the cultivated broth by centrifugation or filtration. If desired, the biomass can be precipitated or flocculated prior to centrifugation or filtration to facilitate separation. Suitable precipitating or flocculating agents are neutral compounds such as alcohols, ketones, ethers and ionic compounds such as quaternary ammonium salts. The biomass thus recovered can be associated with or substantially free from the biopolymer. The method of recovery can be selected to obtain the required product. Thus, for example, a method involving centrifugation can be operated to yield biomass which is substantially free of biopolymer. On the other hand the precipitation technique can give a product comprising biomass associated with the biopolymer.

The biomass which can be either associated with or substantially free from the biopolymer is rich in proteinaceous material and is suitable for use as an animal feedstuff. The processing properties of the biomass can be modified by the amount of the biopolymer present. For example biomass containing 0.5 to 15.0 percent by weight of the polymer can be readily processed in the absence of binding agents such as gluten or flour which are normally used in the formation of structured products which closely resemble meat and to maintain the structure of the textured single cell protein thus formed. The biomass can contain a pink/red pigment which resembles the colour of red meat. Methylomonas strain NCIB number 11221 contains a particularly suitable pink/red pigment. The pigmented biomass can be processed to give a structured product having the appearance of red meat. The structured product can be subjected to a heat treatment such as that used in canning operations or it can be cooked without loss of structure to give a product which simulates the appearance of cooked red meat.

Methods for recovering polyanionic materials and in particular polysaccharide polymers from aqueous solutions are known. The known methods can be used to recover the heteropolysaccharide biopolymer of the present invention from aqueous solutions thereof. The biopolymer can be recovered from the cultivated broth by precipitation and filtration or centrifugation. Most suitably the broth can be heated prior to recovery of the polymer to a temperature in the range 40° C. to 160° C. and preferably in the range 50° C. to 90° C. Preferably, at least the bulk of the microbial cells are removed from the broth before the polymer is recovered. Suitable precipitating agents are neutral compounds such as alcohols, ketones and ethers and ionic compounds such as quaternary ammonium salts e.g. cetyltrimethylammonium bromide. Combinations of neutral and ionic compounds can also be used.

The dried polymer can form free flowing powders. The polymer is soluble in water or aqueous salt solutions. Aqueous solutions of the polymer have shear thinning rheological properties and behave as a pseudoplastic or power law liquid over a wide range of applied shear rates. The pseudoplastic properties are retained in the presence of added salts and are stable to changes in pH and temperature.

The commercial product will normally be contaminated with extraneous material such as microbial cells, cell debris and inorganic material. The presence of this material will affect the viscosity values of aqueous solutions of the product. The intended use will determine the quantity of extraneous material present.

Chemical analysis of the polymer shows that the principal sugar residues is glucose. The polymer can contain sugar residues and other than glucose and is polyanionic in character.

An analysis of samples of the polymer gave the following residue content on a weight basis in relation to the total saccharide contact.
Glucose—38 to 48 percent
Fucose—11 to 20 percent
Mannose—7 to 21 percent
Galactose—11 to 18 percent
Uronic acid—10 to 20 percent
and more particularly
Glucose—38 to 48 percent
Fucose—16 to 20 percent
Mannose—6.5 to 12 percent.
Galactose—12 to 18 percent
Uronic acid—10 to 19 percent It is thought that the saccharide residues are principally linked in a $\beta$ configuration. The heteropolysaccharides can have molecular weights in the range $5.0 \times 10^5$ to $2.0 \times 10^8$ and preferably in the range $1.0 \times 10^6$ to $200 \times 10^6$ when measured by a gel permeation chromatographic technique. The polymer normally has a specific rotation $[\alpha]_{20}$ of less than 10°.

The polymer can be used as a rheological modifier or a thickening or suspending agent in a wide range of applications such as for example in oil-well drilling-mud formulations, enhanced oil recovery compositions, emulsion stabilizers, liquid drag reducing agents, and thickening and suspending agents in foods, cosmetics and paints. In addition the polymer can be used as an adhesive, a water soluble packaging film or a water soluble encapsulating material.

The present invention is further described in the following Examples.

EXAMPLE 1

20 liters of an aqueous nutrient medium having the composition given below were added to a fermenter having a total capacity of 30 liters. The fermenter was equipped with an impeller for agitating the broth and means for aerating and supplying methane to the broth.

Aqueous nutrient medium $H_3PO_4$—100.0 milligrams
$H_2SO_4$—4.0 milligrams
$HNO_3$—388.0 milligrams
$K_2SO_4$—28.0 milligrams
$MgSO_4.7H_2O$—53.0 milligrams
$Ca(NO_3)_2.4H_2O$—20.0 milligrams
$CuSO_4.5H_2O$—1.6 milligrams
$FeSO_4.7H_2O$—2.4 milligrams
$ZnSO_4.7H_2O$—0.9 milligrams
$MnSO_4.H_2O$—0.16 milligrams
$Co(NO_3)_2.6H_2O$—0.14 milligrams
$Na_2MoO_4.2H_2O$—0.44 milligrams
$NiCl_2.6H_2O$—0.01 milligrams
$H_3BO_3$—0.20 milligrams
Distilled water to—1 liter The medium was stirred at an impeller speed of 500 rpm. The pH was adjusted to and maintained at 6.6 by means of an automatic titration device by addition of 2.0 N aqueous sodium hydroxide. The temperature was controlled at 30° C. and air and methane were supplied at rates of 3 vol/vol hour and 150 vol/vol hour respectively. A dilution rate of 0.05 $h^{-1}$ was achieved by taking off medium at a rate of 1.0 liter/hour and maintaining a constant working volume in the fermenter by adding fresh aqueous nutrient medium. The air and methane fed to the fermenter were not sterilised and operation was non aseptic.

The fermenter was inoculated at daily intervals over a period of 7 days with 100 milliliter quantities of a series of separately prepared samples which it was thought likely to contain methane utilising micro-organisms. The samples were prepared in the following manner. About 5 milliliter samples of soil, pond mud and pond water obtained from sources where methane utilising micro-organisms could be expected to be found were added to 100 milliliters of "NMS" medium. The "NMS" medium was prepared according to the recipe given by Whittenbury et al in the Journal of General Microbiology 1970, Vol. 61, pages 205-20. Each flask was then fitted with a "Subaseal" stopper. 50 milliliters of air in the flask were replaced by means of a syringe with 50 milliliters of methane. The flasks were then incubated on a rotary shaker at 30° C. for about one week. The gas phase in the flasks was renewed every 2-3 days.

After one week, there was microbial growth in the medium in the fermenter. Over the following several days the methane input rate was reduced and the air input rate, the agitation speed, the dilution rate, the fermenter pressure and the concentrations of salts in the mineral medium supplied to the fermentation were increased progressively to give an air input rate of 120 vol/vol h, a methane input rate of 0.075 $h^{-1}$, a fermenter pressure of 0.7 bar gauge and a nutrient salt concentration in the medium of 18 times that of the original. During the period over which these changes were made the dissolved oxygen concentration of the broth was not allowed to rise above a value corresponding to about 10 percent of air-saturation. A steady-state fermentation was achieved under these conditions. The broth was pink/red in colour and viscous. The concentration of microbial cells was about 12.0 grams dry weight per liter.

A sample of the broth was subjected to centrifugation at 30,000 g for 3 hours to give on the one hand a solid pink to red coloured fraction consisting essentially of microbial cells with some heteropolysaccharide biopolymer and on the other hand an aqueous supernatant liquid which was viscous and almost colourless. The supernatant liquid contained a soluble heteropolysaccharide biopolymer which was precipitated by the addition of a polar solvent such as isopropanol, ethanol or acetone.

After steady-state operation for about 500 hours, a sample of broth taken directly from the fermenter was inoculated onto an "NMS" agar slope and incubated in a gas-tight plastic box containing a 1:4 methane/air atmosphere, at 30° C. for 7 days. A mixed culture consisting of at least one methane-utilising biopolymer forming micro-organism developed on the slope. The culture was pink to red in colour and mucoid in appearance. A subculture of this mixed culture was deposited with the National Culture for Industrial Bacteria (NCIB), Aberdeen, Scotland, where it was assigned the number NCIB 11253.

An analysis of the mixed culture NCIB 11253 showed it to comprise mainly a methane and elemental nitrogen utilising heteropolysaccharide biopolymer forming strain of Methylomonas which was identified as strain NCIB 11221 and a mixture of heterotrophic bacteria including at least one strain of Flavobacterium, a strain of Pseudomonas maltophilia and several unidentified strains resembling species of Pseudomonas and Alcaligenes.

An analysis of the micro-organisms present in the broth at the time that the sample was taken gave 80 percent by number of a methane and elemental nitrogen utilising and biopolymer forming bacterium identified as a strain of Methylomonas a subculture of which was deposited with the NCIB where it was assigned the number NCIB 11221. About 20 percent by number of the micro-organisms present consisted of a mixture of heterotrophic bacteria. Two strains isolated from this mixture were a strain of Flavobacterium and a strain of Pseudomonas. A subculture of each of these bacterial strains was deposited with the NCIB where they were assigned the numbers NCIB 11229 and 11230 respectively.

Each of the bacterial strains mentioned above was isolated in pure culture. The methane-utilising and biopolymer forming bacterium Methylomonas sp. NCIB 11221 was cultivated, characterised and identified according to the methods described by Whittenbury et al in the Journal of General Microbiology (1970), Vol. 61, pages 205–218. The data thus obtained is given in Table 1. The heterotrophic bacteria were identified according to the methods described in Bergey's Manual of Determinative Bacteriology (8th Edition). The data thus obtained is given in Table 2.

TABLE 1

Characteristics of obligate methane utilising bacterium NCIB 11221 isolated from the fermenter at dilution rates of 0.03 and 0.075 hours$^{-1}$ in accordance with the procedure described above.

| | |
|---|---|
| Miscroscopical appearance | Cocco-bacillus 1.5 × 2.5 |
| Motility | + |
| Gram reaction | − |
| Rosette formation* | − |
| Growth on NMS agar with 0.1% (w/v) methanol | + |
| Growth on NMS agar with 0.5% (w/v) glucose | − |
| Colony colour | Pink/red |
| Membrane type and arrangement* | Type I (discs) |
| Growth at 37° C. | − |
| Growth at 45° C. | − |
| Utilisation of elemental Nitrogen | + |
| Pellicle formation in static NMS liquid culture | + |
| G & C Ratio (percent) | 55 ± 2% |

*As described by Davies and Whittenbury J. Gen Microbiol (1970) 61, 227–232.

The data in the table strongly suggests that strain number 11221 can be classified as a member of the species Methylomonas methanica. However strain number 11221 differs from the description of all known strains of M. methanica in its ability to utilise elemental nitrogen as a nitrogen source.

TABLE 2

Characteristics of the heterotrophic bacteria strains NCIB 11229, 11230 and 11231 isolated from the fermenter at a dilution rate of 0.075 hours$^{-1}$ in accordance with the procedure hereinbefore described.

| | NCIB 11229 | NCIB 11230 |
|---|---|---|
| 1. Microscopical appearance | Rods 0.75 μm × 3–5 μm | Rods 0.5 μm × 5 μm |
| 2. Colony morphology and size after 24 hours incubation on NA | Yellow/orange opaque colonies 3mm diameter | Small/white colourless colonies 1mm diameter |
| 3. Gram stain | − | − |
| 4. Motility and flagellation | − | + single polar flagellum |
| 5. Anaerobic growth on NA | − | − |
| 6. Growth on NMS agar containing 0.1% (w/v) methanol | − | − |
| 7. Oxidase test (plate method) | + | + |
| 8. Catalase test | + | v |
| 9. Urease test (Christensen's) | − | − |
| 10. Growth in KCN medium (Møller) | − | − |
| 11. Gelatin liquefaction | + | − |
| 12. Nitrate reduction | − | + |
| 13. Citrate utilisation (Kosers) | − | − |
| 14. Malonate utilisation | NT | + |
| 15. MR test | − | − |
| 16. VP test | − | − |
| 17. Indole test (Kovac's Reagent) | − | − |
| 18. H$_2$S from peptone water | − | + |
| Growth in peptone water sugar media: | | |
| 19. Glucose | − | − |
| 20. Sucrose | − | − |
| 21. Lactose | − | − |
| 22. Maltose | − | − |
| 23. Mannitol | − | − |
| 24. Dulcitol | − | − |
| 25. Adonitol | NT | NT |
| 26. Arabinose | NT | NT |
| 27. Inositol | NT | NT |
| 28. Sorbitol | NT | NT |
| 29. Treholose | NT | NT |
| 30. Xylose | NT | NT |

All tests incubated at 30° C.
+ = positive reaction
− = negative reaction
v = variable
NT = not tested
NA = Nutrient agar
NMS = nitrate mineral salts medium.

EXAMPLE 2

4.5 liters of an aqueous nutrient medium having the following composition were added to a fermenter having a total capacity of 7 liters.

Aqueous nutrient medium $H_3PO_4$—100.0 milligrams
$H_2SO_4$—4.0 milligrams $HNO_3$—388.0 milligrams
$K_2SO_4$—28.0 milligrams
$MgSO_4.7H_2O$—53.0 milligrams
$Ca(NO_3)_2.4H_2O$—20.0 milligrams
$CuSO_4.5H_2O$—1.6 milligrams
$FeSO_4.7H_2O$—2.4 milligrams
$ZnSO_4.7H_2O$—0.9 milligrams
$MnSO_4.H_2O$—0.16 milligrams
$Co(NO_3)_2.6H_2O$—0.14 milligrams
$Na_2MoO_4.2H_2O$—0.44 milligrams
$NiCl_2.6H_2O$—0.01 milligrams
$H_3BO_3$—0.20 milligrams
Distilled water to—1 liter The fermenter was equipped with an impeller for agitating the broth and means for aerating and for supplying methane to the broth.

The medium was stirred at an impeller speed of 1000 rpm, heated to, and maintained at a temperature of 30° C. The pH was adjusted to, and maintained at, 6.7 by the addition of 2 N NaOH by means of an automatic titration device. The fermenter was then seeded with 500 ml of an inoculum, prepared in accordance with the following procedure; 5 flasks each containing 100 ml of sterile NMS liquid medium were inoculated individually with one heavy loopful of mixed culture number NCIB 11253 grown on the surface of an NMS agar slope. Each flask was fitted with a "Subaseal" stopper, gassed with a mixture of 20 percent by volume of methane in air, and incubated on a rotary shaker at 30° C. for 3–4 days.

Immediately after inoculation the medium was slightly turbid. Methane was supplied to the fermenter at a rate of 75 liters/h (15 vol/vol/h) and air was supplied at a rate less than 1 liter/h, such that the dissolved oxygen concentration in the medium, as recorded by a dissolved oxygen probe (LH Engineering Company) was not more than about 20 percent of air saturation. Cultivation was non aseptic using batch conditions. After 24 hours the density of microbial cells began to increase slightly, and the dissolved oxygen concentration began to fall. At this stage the air input rate was increased to 30 liters/hour (6 vol/vol h). After a further 8 hours the impeller speed was increased to 1500 rpm and continuous operation was commenced by supplying the aqueous mineral medium hereinafter described to the fermenter at a rate of 150 ml/hour and removing broth from the fermenter at the same rate to maintain a constant working volume of 5 liters. This resulted in a dilution rate of about 0.03 hours$^{-1}$.

Aqueous nutrient medium $H_3PO_4$—1600 milligrams
$H_2SO_4$—64 milligrams
$HNO_3$—6208 milligrams
$K_2SO_4$—448 milligrams
$MgSO_4.7H_2O$—848 milligrams
$Ca(NO_3)_2.4H_2O$—320 milligrams
$CuSO_4.5H_2O$—25 milligrams
$FeSO_4.7H_2O$—38 milligrams
$ZnSO_4.7H_2O$—14.5 milligrams
$MnSO_4.H_2O$—2.5 milligrams
$Co(NO_3)_2.6H_2O$—2.3 milligrams
$Na_2MoO_4.2H_2O$—7.0 milligrams
$NiCl_2.6H_2O$—0.2 milligrams
$H_3BO_3$—3.0 milligrams
Distilled water to—1 liter Over the next 60 hours of continuous operation the air input rate was progressively increased to 220 liters/h (44 vol/vol h), the methane input rate was progressively decreased to 40 liters/hour (8 vol/vol h), and the impeller speed was increased to 2000 rpm. The pH of the broth was maintained at 6.7 by the addition of 2 N sodium hydroxide and the temperature was controlled at 30° C. Steady-state continuous culture was established under these conditions. The broth was very viscous and pink/red in colour. The gum was produced at a rate of 0.1 grams/liter hour and the microbial biomass at a rate of 0.27 grams/liter hour to give a combined productivity of biopolymer and biomass of 0.37 grams/liter hour.

Broth from the fermenter was collected and passed to a high speed centrifuge operated at 25000 g. Centrifugation of the broth at 25000 g for 3 hours gave on the one hand a clear, viscous liquid containing heteropolysaccharide biopolymer and on the other hand a red/pink pellet of microbial biomass containing some biopolymer.

An analysis of the microbial population present in the broth under steady state conditions of culture showed that it consisted of about 80 percent by a number of cells of the methane utilising and biopolymer forming microorganism Methylomonas NCIB 11221 and 20 percent by number of cells of a mixture of heterotrophic bacteria. About 50 percent by number of the heterotrophic bacteria were small motile, strictly aerobic Gram-negative rods, so far unifentified. A subculture was lodged with the NCIB under the number NCIB 11256. About 30 percent by number of these bacteria were a strain of Flavobacterium sp. NCIB 11229 previously described in Example 1, and about 5 percent by number were motile, strictly aerobic Gram-negative rods, also so far unidentified. A subculture was lodged with the NCIB under the number NCIB 11258. The remaining approximately 15 percent by number consisted of a mixture of bacteria which included strains of Flavobacterium sp., *Pseudomonas maltophilia,* and Pseudomonas sp.

Subcultures of the Flavobacterium sp., *Pseudomonas maltophilia* and Pseudomonas sp., were lodged with the NCIB under the numbers NCIB 11254, 11255 and 11257 respectively.

A very small number of other heterotrophic bacteria were also present but they were not isolated for identification purposes. The data obtained from the various diagnostic tests carried out on the bacterial strains isolated from the broth is shown in Tables 1 to 3.

Comparison of the results from Examples 1 and 2 shows that in continuous culture at dilution rates of both 0.03 h$^{-1}$ and 0.075 h$^{-1}$, the dominant microorganism was the methane utilising and heteropolysaccharide polymer forming strain of Methylomonas sp. NCIB No. 11221 and one of the dominant heterotrophic bacteria was Flavobacterium sp. NCIB No. 11229. The other heterotrophic bacteria in the culture can vary with the actual fermentation conditions but are stable for a particular set of conditions and are selected by the fermentation conditions.

TABLE 3

CHARACTERISTICS OF THE HETEROTROPHIC BACTERIA STRAINS NCIB 11229, 11254, 11255, 11256, 11257 and 11258 ISOLATED FROM THE FERMENTER OPERATED CONTINUOUSLY AT STEADY STATE CONDITIONS AS DESCRIBED IN EXAMPLE 2.

| | NCIB 11229 | NCIB 11254 | NCIB 11255 | NCIB 11256 | NCIB 11257 | NCIB 11258 |
|---|---|---|---|---|---|---|
| 1. Microscopical appearance | Rods 0.75 × 3/5 μm | Rods 1 × 5 μm | Rods 1-5 μm | Rods 0.5 × 2 μm | Curved rods 1 × 4 μm | Rods 1 × 3-4 μm |
| 2. Colony morphology and size after 48 hours on NA | Yellow/orange opaque colonies 3 mm diameter | Yellow/orange translucent colonies 3 mm diameter | Rough lemon colonies 2 mm diameter | Colourless pinpoint colonies | Rough white colonies 1-2 mm diameter | Shiny round lemon colonies 2 mm diameter |
| 3. Gram stain | − | − | − | − | − | − |
| 4. Motility and Flagellation | − | − | + 2 polar flagella | + | + | + |
| 5. Anaerobic growth on NA | − | − | − | − | − | − |
| 6. Oxidase test (Plate method) | + | + | − | + | + | + |
| 7. Catalase test | + | + | + | + | + | + |
| 8. Gelatin liquefaction | + | + | + | 0 | − | + |
| 9. Nitrate reduction | − | − | − | 0 | − | + |
| 10. Citrate utilisation (Kosers) | − | − | − | − | − | − |
| 11. Malonate utilisation | NT | NT | NT | NT | NT | − |
| 12. MR test | − | − | − | 0 | − | − |
| 13. VP test | − | − | − | 0 | − | − |
| 14. Indole test (Kovac's Reagent) | − | − | − | 0 | − | − |
| 15. H$_2$S from TSI | − | + | − | − | − | − |
| 16. Acid from purple milk | NT | NT | − | NT | NT | − |
| 17. Growth in peptone - glucose water sugar media: | − | − | | 0 | + | − |
| sucrose | − | − | − | 0 | − | − |
| lactose | − | − | − | 0 | − | − |
| mannitol | − | − | − | 0 | − | − |
| dulcitol | − | − | − | 0 | − | − |

All tests incubated at 30° C.
+ = positive reaction.
− = negative reaction.
NT = not tested. 0 TSI = Difco triple sugar ion agar.
NA = Nutrient agar.

The meat-like properties of the microbial biomass were assessed in accordance with the following procedure. About 2 liters of the broth described above, were centrifuged at 33,000 g for 3 hours in an MSE High Speed 25 refrigerated centrifuge to give a solid fraction consisting essentially of microbial cells associated with some heteropolysaccharide biopolymer. The solid was freeze-dried using a Serail CS12 freeze drier. This freeze-dried solid was found to contain about 95 percent by weight of biomass and about 5 percent of the biopolymer. 5 g of the solid were processed to form a dark red textured mass. The mass was cut into 3 millimeter cubes, suspended in distilled water and cooked in a pressure cooker (15 psig) for 15 minutes. After cooling to room temperature, examination of the cubes showed that they had retained their structure with a 2-3 fold increase in size. The structured chucks had a lean meat-like appearance. The cooled cubes were stable to vigorous shaking.

The heteropolysaccharide biopolymer formed during the fermentation was isolated and characterised in accordance with the following procedure.

12 liters of the broth containing biomass and biopolymer produced under steady state conditions of continuous culture as herein described in this example were diluted with 12 liters of water and passed at a rate of 75 cm$^3$ minute$^{-1}$ through a Sharples Type 16 centrifuge operated at 17,000 g to remove most of the biomass (bacterial cells). 11 liters of the supernatant liquid recovered after removal of biomass were freeze-dried using a "Serail CS12" freeze drier. 25 grams of a buff solid heteropolysaccharide biopolymer were obtained. The sample was designated as Sample 1.

The freeze-dried biopolymer was made up in sea water to give a 0.24 percent w/v solution. The viscosity of the solution was measured using a Brookfield Viscometer (UL attachment) at 30° C. The viscosity characteristics thus obtained are given in Table 4.

The viscosity characteristics of the biopolymer sample 1 were then tested in accordance with the following procedure in typical oil well drilling formulations.

Biopolymer sample 1 was incorporated into a typical drilling mud to give the following composition.

Formulation 1

Sea water—350 cm$^3$
Sodium carbonate—2.5 g
Bentonite—5.0 g
Potassium chloride—35 g
Dextrid—3 g
Low viscosity carboxymethyl cellulose (LV-CMC)—2 g
Bipolymer sample 1—2.5 g The pH of the mud was 9.3. The viscosity was measured using a Fann V-G Viscometer. The data thus obtained is given in Table 5.

Formulation 2

A second oil drilling mud formulation was prepared from biopolymer sample 1 in accordance with the composition given above for Formulation 1, except that sodium hydroxide (0.5 g) was added to raise the pH to 9.9.

The viscosity was measured using a Fann V-G Viscometer. The data thus obtained is given in Table 5. The data shows that the biopolymer is a suitable material for inclusion in oil well drilling mud formulations.

TABLE 5

| Test | Formulation 1 | Formulation 2 |
|---|---|---|
| Apparent viscosity centipoise | 23 | 21.5 |
| Plastic viscosity centipoise | 16 | 15 |

TABLE 5-continued

| Test | Formulation 1 | Formulation 2 |
| --- | --- | --- |
| Yield point lbs/100 sq ft Initial/Ten minute | 14 | 13 |
| Gel strength lbs/100 sq ft | ⅛ | ⅛ |

A second sample of the biopolymer was recovered from the broth and its viscosity characteristics assessed in the following manner.

About 6 liters of the broth were centrifuged at 33,000 g for 3 hours in an MSE High Speed 25 refrigerated centrifuge. 4 liters of the supernatant liquid recovered after removal of the biomass were concentrated to 1 liter under reduced pressure in a rotary evaporator. 2 liters of iso-propanol were added with vigorous agitation to the concentrate to precipitate the polymer. The precipitated material was separated from the supernatant liquid by centrifugation, washed with aqueous iso-propanol (90% v/v) and dried in vacuo to give 7.5 g of a white/buff powder of polymer which was designated as Sample 2.

The powder was made up in sea water to give 0.54 percent solution of the polymer. The viscosity of the solution was measured using a Brookfield Viscometer (UL attachment) at 30° C. The viscosity characteristics thus obtained are given in Table 4.

TABLE 4

| | Viscosity - centipoise | |
| --- | --- | --- |
| Shear Rate - seconds$^{-1}$ | Sample 1 0.24% solution | Sample 2 0.54% solution |
| 7.2 | 7.6 | 26.5 |
| 14.4 | 6.6 | 23.6 |
| 36.0 | 5.6 | 19.4 |
| 72.0 | 4.9 | OFF SCALE |

A further sample (Sample 3) of the polymer was recovered from the broth and its shear characteristics in aqueous solution assessed in the following manner.

1.2 liters of the broth were centrifuged at 33,000 g for 2.5 hours in an MSE High Speed refrigerated centrifuge. 300 cm$^3$ of the supernatant liquid were concentrated ten-fold and freeze-dried in a "Serail CS12" freeze drier. A portion of the freeze-dried polymer was dissolved in sea water (0.4 percent weight/vol) and the viscosity measured using a Weissenberg Rheogonimeter.

The data obtained is shown in graphical form in the Figure which demonstrates that the polymer in aqueous solutions when subjected to a wide range of applied shear rates behaves as a pseudoplastic or a power law liquid.

EXAMPLE 3

Further samples of the biopolymer were isolated from broths produced in accordance with the techniques described in Example 2. The samples were designated as 4 to 6. A quantity of the sample 4 was made up with sea water to give a 0.75 percent weight/vol solution. The viscosity of the solution was then measured at a series of increasing and decreasing shear rates in a Haake Rotovisco Viscometer using the standard NV1 bob and cup system. The data thus obtained is given in Table 6.

TABLE 6

| | Viscosity (centipoise) | |
| --- | --- | --- |
| Shear Rate | Increasing Shear Rate | Decreasing Shear Rate |
| 291 | 72 | 72 |
| 437 | 60 | 60 |
| 873 | 42 | 43 |
| 1310 | 35 | 35 |
| 2620 | 24 | 24 |

This data demonstrates the reversible shear thinning characteristics of the aqueous solution of the polymer.

The optical rotation of a quantity of sample 5 was measured using a Hilger Polarimeter. The value of the specific rotation $[\alpha]_{20}°$ was $-26°$.

Molecular weight determinations were carried out on a sample 6 using the known gel permeation chromotography technique and a Waters GPC/ALC—244 chromatograph fitted with five 2 foot × ⅜ inch columns connected in series and packed with porous glass substrate with 2000, 1250, 700, 240 and 75 Å pore diameters respectively. The apparatus was calibrated using standard Dextran Fractions. The polymer was found to have two major heteropolysaccharide fractions having average molecular weights of about $110 \times 10^6$ and $2 \times 10^6$ respectively.

EXAMPLE 4

6 samples of the heteropolysaccharide polymer were recovered from fermentation broths prepared in accordance with the techniques described in Example 2. The saccharide contents were analysed in the following manner.

The samples were hydrolysed at 100° C. for 20 hours in 1 N sulphuric acid. The hydrolysate was neutralised with barium hydroxide and the precipitated barium sulphate removed by centrifugation. The principal saccharides present in the hydrolysate were identified by gas chromatography and mass spectrometry of their per-acetyl derivatives as glucose, fuccose, mannose and galactose. The presence of an uronic acid was shown, by thin layer chromatography. The linkage configurations were not determined, however they are thought to be mainly in the $\beta$ configuration.

A quantitative analysis of the saccharides and the uronic acid present in the samples is given in Table 7.

TABLE 7

| Mono Saccharide Residue | Relative Composition (% w/w) of Carbohydrate Fraction of the polymer | | |
| --- | --- | --- | --- |
| | Mean Value (5 samples) | Range (5 samples) | Odd sample |
| Glucose | 43.0 | 39.1 to 47.4 | 38.5 |
| Fucose | 18.9 | 16.5 to 19.7 | 11.3 |
| Mannose | 8.5 | 7.0 to 11.3 | 20.1 |
| Galactose | 15.1 | 12.4 to 17.4 | 11.0 |
| Uronic Acid | 14.6 | 10.8 to 18.7 | 19.1 |

It can be seen from the table that one sample had a substantially different composition with respect to the fucose and mannose content compared with the remaining 5 samples. The confidence limits for the quantitative figures for the saccharides were not estimated.

EXAMPLE 5

This example illustrates a 2-stage fermentation system favouring the production of heteropolysaccharide biopolymer.

In a first stage 6.0 liters of a fermentation broth produced in accordance with the technique described in Example 2 was placed in a fermenter having a total capacity of 7 liters. The broth contained approximately 80 percent by number of cells of Methylomonas NCIB 11221 and approximately 20 percent by number of cells of a mixture of heterotrophic bacteria. The total cell concentration in the broth sample was about 9 grams per liter (dry weight basis).

The fermenter was equipped with an impeller and means for supplying air and methane to the broth.

The broth was stirred at an impeller speed of 1000 rpm, heated to, and maintained at a temperature of 30° C. The pH was adjusted to and maintained at 6.4, using 2.0 N sodium hydroxide solution which was added by means of an automatic pH controller. Methane was supplied to the broth at a rate of 40 liters per hour and air was supplied at a rate of between 10 and 100 liters per hour such that the dissolved oxygen concentration in the broth as recorded by a dissolved oxygen probe (LH Engineering Company) was not more than about 10 percent of air saturation. An aqueous mineral medium was supplied to the broth at a rate of 600 ml per hour and broth was removed from the fermenter at a similar rate to maintain a constant working volume of 6.0 liters. This resulted in a dilution rate of $0.1\ h^{-1}$. The composition of the aqueous nutrient medium was as follows:

1st Stage Aqueous Nutrient Medium $H_3PO_4$—800 milligrams
$H_2SO_4$—34 milligrams
$HNO_3$—3000 milligrams
KCl—191 milligrams
$MgSO_4.7H_2O$—426 milligrams
$CaCl_2$(Anhydrous)—75 milligrams
$CuSO_4.5H_2O$—12.6 milligrams
$FeSO_4.7H_2O$—19.0 milligrams
$ZnSO_4.7H_2O$—7.3 milligrams
$MnSO_4.H_2O$—1.2 milligrams
$CoCl_2.6H_2O$—1.0 milligrams
$Na_2MoO_4.2H_2O$—3.4 milligrams
Distilled water—to one liter Over the first 24 hours of continuous cultivation, the air input rate was progressively increased to 220 liters per hour, keeping the level of dissolved oxygen in the broth below 10 percent of air saturation. After 5 days under these conditions steady-state non-aseptic continuous operation was established. The broth produced from this fermentation was pink/red in colour and very slightly viscous. The broth was centrifuged 2 hours and an analysis of the supernatant liquor showed it to have a total carbohydrate concentration (anthrone method) of 40 mg/liter. This broth ws then passed to the second-stage fermenter in which it was subjected to the following batch condition of cultivatiom.

15 liters of an aqueous nutrient medium having the composition given below were added to a fermenter having a total capacity of 30 liters. The fermenter was equipped with an impeller and with a means of supplying methane and air.

2nd Stage Aqueous Nutrient Medium $H_3PO_4$—530 milligrams
$H_2SO_4$—22 milligrams
$HNO_3$—2000 milligrams
$K_2SO_4$—150 milligrams
$MgSO_4.7H_2O$—284 milligrams
$CaCl_2$(anhydrous)—50 milligrams
$CuSO_4.5H_2O$—8.4 milligrams
$FeSO_4.7H_2O$—13.0 milligrams
$ZnSO_4.7H_2O$—5.0 milligrams
$MnSO_4.H_2O$—0.8 milligrams
$CoCl_2.6H_2O$—0.7 milligrams
$Na_2MoO_4.2H_2O$—2.3 milligrams
Distilled water—to—one liter The medium was stirred at an impeller speed of 1000 rpm and heated to 30° C. The pH of the medium was adjusted to 6.0 using 2.0 N sodium hydroxide. 5 liters of the culture broth from the first stage continuous fermentation described above were added to the medium within the fermenter. Air was suppled at 25 liters/minute and methane at 6 liters/minute. The impeller speed was maintained at 1000 rpm. The pH was measured but not controlled. No further additions to the fermenter were made.

In this batch cultivation the initial cell density was about 3 g/liter (dry weight basis). The cell density was 11 g/liter at 22 hours and remained at this density until fermentation was terminated at 46 hours.

The quantity of nitrate present in the broth was measured at intervals. At 22 hours no nitrate was detected. Growth was limited by restriction of the nitrogen source.

Fermentation was continued for 46 hours under non-aseptic conditions during which time the broth became very viscous. Viscosity was measured using a Brookfield viscometer model No. LVF fitted with bob No. 3 turning at 6 rpm. The initial viscosity immediately after the fermentation was inoculated was too low to be measured by the viscometer set up as described above, but after 22 hours the viscosity was found to be 4900 centipoises and after 46 hours the viscosity had risen to 10 700 centipoises. The total saccharide content in the supernatant liquor after centrifugation of the broth was found to be 1550 mg/liter after 22 hours and 2200 mg/liter after 46 hours. This indicated that the increase in viscosity was due to the presence of a water-soluble extracellular polysaccharide.

At the end of the second stage fermentation (i.e. after 46 hours) the broth was pasteurised by turning off the methane and air supplies to the broth and rapidly increasing the termperature from 30° C. to 60° C. After 10 minutes, the broth was rapidly cooled to 30° C.

The polymer was recovered from the cooled broth by the following technique:

16 liters of the heat treated and cooled broth were diluted with 4 volumes of distilled water and centrifuged in a continuous Sharples super centrifuge (Model 16) using a flow rate of about 80 $cm^3\ min^{-1}$.

60 liters of the centrifuged supernatant liquor were transferred to a stainless steel vessel and a substantially cell free polysaccharide was precipitated by the addition of potassium choride to give a 2 percent w/v solution and 120 liters of methanol. The precipitated material was separated by centrifugation (Alfa Laval 102B-25 centrifuge) and redissolved in 2 liters of distilled water. The product was re-precipitated by the addition of potassium chloride to give a 2 percent w/v solution and 4 liters of methanol.

The polymer was separated by centrifugation and dehydrated (twice) with 2 liters of methanol and separated by filtration. The polymer was air dried and ground in a hammer mill to yield a buff free flowing powder. An analysis of the polymer gave:

| Moisture | 14.0 percent w/w |
|---|---|
| C | 45.5 percent w/w |
| H | 5.4 percent w/w |
| N | 3.3 percent w/w |
| Ash | 6.7 percent w/w |

The viscosity of a 1 percent solution in distilled water was measured using a Ferranti Shirley viscometer. This showed a viscosity of 268 centipoises at a shear rate of 100 sec$^{-1}$, and 58 centipoises at 1000 sec$^{-1}$.

We claim:

1. A polyanionic heteropolysaccharide biopolymer having molecular weight in the range of $5.0 \times 10^5$ to $2.0 \times 10^8$ when measured by gel permeation chromatography and comprising the saccharide residues glucose, fucose, mannose, galactose and uronic acid in the following proportions based on weight of total saccharide content: from 38 to 48% glucose; from 11 to 20% fucose; from 7 to 21% mannose; from 11 to 18% galactose and from 10 to 20% uronic acid.

* * * * *